(12) United States Patent
Chamney et al.

(10) Patent No.: US 9,186,448 B2
(45) Date of Patent: Nov. 17, 2015

(54) METHOD FOR CONTROLLING OF A FILTRATION RATE, CONTROLLER, AND DEVICES

(75) Inventors: Paul Chamney, Herts (GB); Ulrich Moissl, Karben (DE); Peter Wabel, Darmstadt (DE); Sebastian Wieskotten, Ober-Ramstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 382 days.

(21) Appl. No.: 13/642,636

(22) PCT Filed: Apr. 15, 2011

(86) PCT No.: PCT/EP2011/101913
§ 371 (c)(1),
(2), (4) Date: Dec. 3, 2012

(87) PCT Pub. No.: WO2011/131319
PCT Pub. Date: Oct. 27, 2011

(65) Prior Publication Data
US 2013/0081998 A1    Apr. 4, 2013

Related U.S. Application Data

(60) Provisional application No. 61/346,048, filed on May 19, 2010.

(30) Foreign Application Priority Data

Apr. 22, 2010  (EP) .................................... 10004270
May 19, 2010  (EP) .................................... 10005212

(51) Int. Cl.
*A61M 1/16*    (2006.01)
*A61M 1/34*    (2006.01)
(Continued)

(52) U.S. Cl.
CPC ............ *A61M 1/1613* (2014.02); *A61B 5/4875* (2013.01); *A61M 1/16* (2013.01);
(Continued)

(58) Field of Classification Search
CPC . A61M 1/161; A61M 1/3609; A61M 1/1613; A61M 2205/52; A61M 2205/50; A61M 2230/20; A61M 2205/33; A61B 5/4875; G06F 19/34
See application file for complete search history.

(56) References Cited

U.S. PATENT DOCUMENTS 6,602,424 B1    8/2003  Kramer et al.
7,072,710 B2 *  7/2006  Chamney ...................... 600/547
(Continued)

FOREIGN PATENT DOCUMENTS

CN    1678360 A    10/2005
EP    1 927 371 A2    6/2008
(Continued)

OTHER PUBLICATIONS

International Search Report from PCT/EP2011/001913 mailed on Jul. 20, 2011.

*Primary Examiner* — John Kim
(74) *Attorney, Agent, or Firm* — Kenyon & Kenyon LLP

(57) ABSTRACT

The present invention relates to a method for controlling a filtration rate during treatment of a body fluid, e.g., during hemofiltration or dialysis, comprising the steps of defining a target relation, or a development during dialysis thereof, between one or more calculated or measured value(s) reflecting the mass, concentration, or the volume of a substance comprised by a patient's tissue or bodily fluid, and one or more calculated or measured value(s) reflecting a patient's distribution space or an approximation thereof; during dialysis repeatedly calculating or measuring value(s) reflecting the mass, concentration or the volume of the substance and/or reflecting the distribution space or an approximation thereof, and determining the relation therebetween at least once; and controlling the filtration rate of the body fluid treatment device such that the determined relation is or approaches the target relation. It also relates to systems for conducting the method, and related computer-readable storage media.

20 Claims, 11 Drawing Sheets

(51) Int. Cl.
  *B01D 61/32* (2006.01)
  *A61M 1/36* (2006.01)
  *A61B 5/00* (2006.01)
  *G06F 19/00* (2011.01)
(52) U.S. Cl.
  CPC ............ *A61M 1/3609* (2014.02); *G06F 19/34* (2013.01); *A61M 2205/33* (2013.01); *A61M 2205/50* (2013.01); *A61M 2205/52* (2013.01); *A61M 2230/20* (2013.01)

(56) References Cited

U.S. PATENT DOCUMENTS 8,551,342 B2 * 10/2013 Moissl et al. ................ 210/739

| | | |
|---|---|---|
| 2007/0215545 A1 | 9/2007 | Bissler et al. |
| 2010/0168925 A1 | 7/2010 | Hilgers et al. |
| 2011/0036773 A1 | 2/2011 | Moissl et al. |

FOREIGN PATENT DOCUMENTS

| | | |
|---|---|---|
| JP | 2011-512212 A | 4/2011 |
| WO | 98/23311 A1 | 6/1998 |
| WO | 02/47609 A2 | 6/2002 |
| WO | 2004/022135 A1 | 3/2004 |
| WO | 2007/140993 A1 | 12/2007 |
| WO | 2009103550 A1 | 8/2009 |

* cited by examiner

METHOD FOR CONTROLLING OF A FILTRATION RATE, CONTROLLER, AND DEVICES

CROSS REFERENCE TO RELATED APPLICATIONS

This is a 371 national phase application of PCT/EP2011/001913 filed Apr. 15, 2011, which claims priority from European Patent Application No. EP 10004270.4, filed Apr. 22, 2010, European Patent Application No. EP 10005212.5, filed May 19, 2010, and U.S. Provisional Patent Application No. 61/346,048, filed May 19, 2010.

FIELD OF INVENTION

The present invention relates to a method for controlling of a filtration rate during treatment of a bodily fluid of a patient by utilization of a bodily fluid treatment device, comprising the step of defining a target relation, or a development thereof during treatment, between one or more calculated or measured value(s) reflecting the mass or the concentration or the volume of a substance comprised by a tissue or a bodily fluid of the patient and reflecting a distribution space of the patient or an approximation thereof, wherein during treatment of the bodily fluid value(s) reflecting the mass or the concentration or the volume of the substance and/or reflecting the distribution space or an approximation thereof are repeatedly calculated or measured, and wherein the relation there between the repeatedly calculated or measured values is determined at least once; and wherein the filtration rate of the fluid treatment device is controlled such that the determined relation is identical or similar to the target relation or approaches it or aims to do so. The present invention also relates to a controller, an apparatus, a device, a digital storage device, a computer program product, and a computer program.

BACKGROUND OF THE INVENTION

Quite frequently, patients have to be treated regarding to their fluid balance by the use bodily fluid treatment devices, e.g., a dialysis apparatus. The present invention aims at providing a method for controlling a filtration rate during dialysis of the patient. Also, the present invention suggests devices applicable in the field or context of filtration rate control.

By utilization of the present invention a method for controlling a filtration rate during bodily fluid treatment by utilization of a device such as a device for blood treatment or dialysis is suggested. Also, a controller for carrying out the method according to the present invention is provided, as well as an apparatus, a device comprising a controller, a digital storage device, a computer program product, and a computer program.

In one aspect of the present invention, a method for controlling of a filtration rate during treatment, in particular blood treatment, and more particular dialysis, of a patient by utilization of a bodily fluid treatment device such as a dialysis device is proposed, comprising the step of defining a target relation, or a development thereof during blood treatment, between one or more calculated or measured value(s) reflecting the mass or the concentration or the volume of a substance comprised by a tissue or the bodily fluid of the patient and reflecting a distribution space of the patient or an approximation thereof, respectively, wherein during treatment or blood treatment, in particular, dialysis value(s) reflecting the mass or the concentration or the volume of the substance and/or reflecting the distribution space or an approximation thereof are repeatedly calculated or measured, and wherein the relation between the repeatedly calculated or measured values is determined at least once; and wherein the filtration rate of the bodily fluid treatment device is controlled such that the determined relation is identical or similar to the target relation or approaches it or aims to be or do so.

The patient can be either a human being or an animal. The patient may be sound or ill. The patient may be in need of medical care or not. The patient may be a dialysis patient or not.

In another aspect of the present invention, a controller is intended or provided or used or configured to carry out the method according to the present invention. The controller optionally comprises system(s) needed and suited and/or configured to carry out the respective steps of the method according to the present invention.

In particular, the controller comprises a target relation defining system configured for defining a target relation, or a development thereof during fluid treatment, between one or more calculated or measured value(s) reflecting the mass or the concentration or the volume of a substance comprised by a tissue or a bodily fluid of the patient, and one or more calculated or measured value(s) reflecting a distribution space of the patient or an approximation thereof; a calculation system configured for, during treatment of the bodily fluid, repeatedly calculating of value(s) reflecting the mass or the concentration or the volume of the substance and/or reflecting the distribution space or an approximation thereof, and determining the relation there between at least once; and a signal output system configured for outputting of one or more signals to a controlling system for controlling the filtration rate of the fluid treatment device such that the determined relation is or approaches the target relation or aims to do or be so.

In yet another aspect of the present invention, an apparatus is provided, the apparatus comprising system(s) for obtaining one or more value(s) reflecting or concerning the distribution space or an approximation or changes thereof of the patient's body, and/or system(s) for obtaining a value reflecting the mass, the volume or the concentration of the substance or changes thereof. The apparatus further comprises at least one controller according to the present invention.

In another aspect of the present invention, the apparatus comprises at least one controller according to the present invention or at least one apparatus according to the present invention.

In another aspect of the present invention, a digital storage device, in particular a disc, CD or DVD, has electrically readable control signals which are able to interact with a programmable computer system such that the method according to the present invention will be executed.

In another aspect of the present invention, a computer program product has a program code stored on a machine readable data medium for executing the method according to the present invention when executing the computer program product on a computer.

In another aspect of the present invention, a computer program has a program code for the execution of a method according to the present invention when executing the program on a computer.

Embodiments can include one or more of the following features.

In some embodiments, the target relation is predetermined or preset.

In certain embodiments, the target relation is defined by a target range or one or more target line(s).

In some embodiments, the target range is a combination of one or more thresholds.

In certain embodiments, the target line or range is a trajectory in a diagram, preferably in a diagram in which a no-refill-curve might also be or is illustrated. Also, preferably, the target line or range is a trajectory in a diagram depicting a value representing the mass, concentration or volume of a substance (or changes thereof) as referred to herein over a distribution space (or changes thereof)—or vice versa.

In some embodiments, the target relation is defined before starting the respective dialysis treatment. In certain embodiments, the target relation is defined during the respective dialysis treatment.

In some embodiments, the controlling of a filtration rate during dialysis is an intentional step. In these embodiments, the result of the control as regards the filtration rate is not to be mixed up with results achieved by chance or at random or in an uncontrolled manner.

In certain embodiments, the method according to the present invention comprises the step of determining or measuring the blood volume BVo in the normohydrated condition (i.e., with a relative overhydration of about 0 liter) of the patient.

In some embodiments, the blood volume BVo can be determined by a body composition measurement using the following equation:

$$BV_0 = 0.1 \times LTM + 0.01 \times ATM \quad (1)$$

with LTM being the lean tissue mass and ATM being the adipose tissue mass. Both LTM and ATM can be measured with monitors available in the market.

In certain embodiments, the blood volume BVo can be determined by the use of a anthropometric blood volume equation. In certain embodiments, the following formula by Nadler et al. is used:

For males:

$$BVo = 0.3669 \times (\text{height of the person at issue in meter})^3 + 0.03219 \times \text{weight of that person in kg} + 0.6041 \quad (1a)$$

For females:

$$BVo = 0.3561 \times \text{height}^3 (\text{in meter}) + 0.03308 \times \text{weight in kg} + 0.1833 \quad (1b)$$

as published in Nadler, S. B., Hidalgo, J. U. and Block, T.: "*Prediction of Blood Volume in Normal Human Adults.*" Surgery, 51, 224-232, 1962.

In some embodiments, the method according to the present invention comprises the step of determining or measuring a maximum-refill curve or steady-state curve of the patient. In certain embodiments, the maximum-refill curve or steady-state curve is one boundary or limit of the target range for the relation.

The course of the maximum-refill curve or steady-state curve of the patient is in certain embodiments calculated or identified as follows:

The concentration c_Hb (also referred to in the following equations as "Hb") of hemoglobin (Hb) depends on the mass m_Hb (or $m_{Hb}$) of Hb and the present blood volume BV of a given point of time as follows:

$$Hb = \frac{m_{Hb}}{BV} \quad (2)$$

BV in turn is the sum of the blood volume BVo at normohydrated conditions and the overhydration volume stored within the blood vessel system. The latter can be calculated by utilization of the slope of the Guyton curve being a curve depicting the blood volume BV over the extracellular fluid volume ECW of a patient explaining physiologic interdependencies between extracellular water (ECW) and the blood volume. The overhydration volume stored within the blood vessel system equals K_Guyton*OH, with K_Guyton being the slope of the Guyton curve:

$$Hb = \frac{m_{Hb}}{BV_0 + k_{Guyton} \times OH} = \frac{1}{\frac{BV_0}{m_{Hb}} + \frac{k_{Guyton}}{m_{Hb}} \times OH} \quad (3)$$

That way, the relation between concentration c_Hb of Hb and the overhydration OH can be expressed by $$Hb = \frac{1}{b + a \times OH} \text{ with } b = \frac{BV_0}{m_{Hb}} \text{ and } a = \frac{k_{Guyton}}{m_{Hb}} \quad (4)$$

Hence, by assessing the patient's hemoglobin concentration c_Hb over overhydration OH or over relative overhydration relOH before starting a dialysis treatment, one will get data that can be used for drafting or approximating the steady-state-curve or maximum-refill curve of that patient before starting a dialysis treatment or at the beginning thereof. As is obvious, the course of that curve can be drafted the more precisely the more constant m_Hb of Hb is for that patient. Also, the steady-state-curve or maximum-refill curve is more precise in the linear sections of the Guyton curve.

As can be seen from equation (4), from the approximated parameter b and by use of BVo, the total mass m_Hb of Hb can be determined; also, from parameter a and the total mass m_Hb of Hb the slope K_Guyton of the curve can be determined.

It is noted that the steady-state curve can be determined, approximated or drawn once two data gained or measured independently from each other or at different time points are known as well as BVo. In all other cases, as few as three data gained form different measurements will do as well.

In certain embodiments, the course of the steady-state curve is approximated based on only two measurement data as follows:

Before dialysis treatment, AEOH_pre and Hb_pre are measured (e.g. by the utilization of monitors commercially available from the present applicant). In certain embodiments, during dialysis treatment, a sufficiently strong UF bolus—that is, a suddenly increased ultrafiltration rate—is applied. In sufficient time before the dialysis treatment is terminated, the ultrafiltration is terminated for achieving a stable value called Hb_post indicating a Hb concentration. Once the refill process has been awaited and taken place, a value for AEOH_post is calculated by use of the ultrafiltration volume UFV. The steady-state curve (as is shown, e.g., in FIG. 1) can be approximated based on AEOH_pre, AEOH_post, Hb_pre, and Hb_post.

In some embodiments, a number of minor boluses is applied yielding the same result as is achieved with one strong bolus.

In certain embodiments, no bolus is applied at all. For example, if the filtration rate is set such that during filtration a maximum refill is achieved, the course of the treatment takes place just on the steady state curve.

In some embodiments, the course of the steady-state curve is approximated based on only two arbitrarily chosen measurement data. One exemplary procedure in which the curve is approximated on just two measurement data can be described as follows:

Before dialysis treatment, AEOH_pre is measured. During dialysis treatment, a rather low ultrafiltration rate is set such that a refill process can be observed or achieved from the onset or the very beginning of the dialysis. From the present ultrafiltration volume UFV and AEOH_pre, the present value for AEOH can be calculated. The present value for Hb can be determined by utilization of the blood volume monitor.

In some embodiments, the at least one value reflecting the mass, the volume or the concentration of the substance was obtained from blood samples.

In certain embodiments, the substance is comprised by the group comprising at least any protein produced naturally in the body of the patient, in particular hemoglobin (short: Hb), albumin, insulin, glucose, c-reactive protein (short: CRP), and non endogeneous substances, in particular pharmaceutically effective substances.

In some embodiments, the mass, the volume or the concentration of the substance or changes thereof is an indicator of the anemia state of the patient.

In certain embodiments, the anemia state of the patient is defined by the utilization of direct or indirect measurements or calculations of the mass, the concentration or the volume of a substance, e.g. hemoglobin (Hb), or changes over time thereof.

In some embodiments, the anemia state of the patient is defined by the utilization of direct or indirect measurements or calculations of the hematocrit (Hct) or changes over time thereof.

In some embodiments, the distribution space of the patient is an either measured or calculated value of the blood volume (BV). In certain embodiments, the distribution space is the blood volume at the beginning of another treatment session including filtration of the blood. In some embodiments, the distribution space is the intravascular blood volume. In certain embodiments, the distribution space and/or the blood volume encompasses the volume of the tube system of an extracorporeal blood system or parts thereof that is/are filled with blood. In certain embodiments, those parts may amount to 100, 150 or more milliliters (ml). For example, those parts comprise 130 ml with the applicant's dialysis device of the 5008 type (and 170 ml when used for Single Needle applications), and 170 ml with the applicant's dialysis device of the 2008 or 4008 type (and 210 ml when used for Single Needle applications). Also, in some embodiments, the blood capacity of the filter is also considered as part of the blood volume and/or the distribution space. The blood volume comprised by the filter may amount to 74 ml (FX60 by Fresenius, Germany) or about 100 ml (FX80 by Fresenius, Germany).

In some embodiments, the distribution space of the patient is an approximation based on either measured or calculated values reflecting the relative overhydration (relOH) of the patient.

In certain embodiments, the distribution space is defined as the ECW (extracellular water), the extracellular volume or fluid, the ICW (intracellular water), the intracellular volume or fluid, the plasma volume, the TBW (total body water), the liquor, the volume of oedema, lymph, urine, or any other bodily fluid or volume, and also combinations thereof. Also, the distribution space within the meaning of the present invention can be any ratio of volumes as mentioned before, e.g. ECW/ICW, etc.

In some embodiments, a target range for the target relation is defined in a diagram reflecting the mass or the concentration of the substance and the distribution space or the approximation thereof.

In certain embodiments, the method comprises the step of calculating a no-refill-curve.

In some embodiments, values that lie on the no-refill-curve are considered as a edge of a target range for the target relation.

In certain embodiments, the no-refill-curve relates to the state (which may change during dialysis and depending on the relative overhydration of the patient treated by dialysis) in which the blood volume is decreased by the same amount as is the (ultra)filtration volume (per time unit). As a result, the blood volume BV decreases quickly, and the Hb concentration c_Hb increases in turn. The no-refill-curve can delimit a no-refill-area (in a figure, for example) or no-refill-condition (in a patient, for example) from a refill-area or a refill-condition.

In some embodiments, the method according to the present invention comprises the step of calculating and/or measuring parameters reflecting the mass or the concentration of the substance and/or the distribution space of the patient or an approximation thereof.

In some embodiments, the method further includes assessing the size of at least one distribution space based on measured values and/or results of calculations reflecting a hemoglobin (Hb) state. The hemoglobin (Hb) state may be reflected by the Hb concentration, its total mass, its volume, change thereof over time, respectively, etc.

In certain embodiments, the method further includes assessing the size of at least one distribution space based on measured values and/or results of calculations reflecting the hematocrit (Hct) or changes thereof over time.

As is evident to the skilled person, the assessment of the size of at least one distribution space is not limited to be based on measured values and/or results of calculations reflecting a hemoglobin (Hb) state or the hematocrit (Hct) or changes thereof. The present invention can of course also be carried out based on measured values and/or results of calculations reflecting a mass, concentration or volume (and changes thereof) of any other suitable substance or marker.

In some embodiments, the method further includes using the size of at least one distribution space as obtained based on results from measurement of blood samples and/or from blood comprised in extracorporeal blood lines by utilization of an appropriate monitor. The measurements can be made by measuring the optical properties of the blood by optical sensors and/or by assessing acoustic properties like transit times and/or propagation velocities of ultrasonic pulses by ultrasonic sensors.

For determining the hydration state also any appropriate monitor can be used, such as monitors based on bioimpedance or dilution techniques.

In certain embodiments, the method further includes using the size of at least one distribution space as obtained based on results from urine samples.

In some embodiments, the method further includes using the size of at least one distribution space as obtained based on results from tissue samples.

In certain embodiments, the method further includes plotting results of the control for visual assessment.

In certain embodiments, the apparatus for controlling of a filtration rate during dialysis comprises a system for obtaining a value reflecting the distribution space or an approximation or changes thereof of the patient's body, and/or a system for obtaining a value reflecting the mass, the volume or the concentration of the substance or changes thereof. In these embodiments, the apparatus comprises at least one controller according to the present invention.

In some embodiments, the apparatus according to the present invention comprises a system for measuring or calculating the distribution space or an approximation or changes thereof, in particular for measuring or calculating the hydration state or an overhydration, or wherein the system for obtaining a value consists of such a system for measuring or calculating.

In certain embodiments, the apparatus comprises a system for obtaining a value reflecting the mass, the volume or the concentration of the substance that comprises at least one of a weight system, a system for determining the blood volume of the patient, a keyboard, a touch screen, a system for measuring or calculating the concentration, the volume and/or the mass of the substance, in particular hemoglobin (Hb) in blood, or changes thereof, or wherein the system for obtaining a value consists of such system for measuring or calculating.

In some embodiments, the apparatus according to the present invention comprises a system configured and intended for determining or assessing the relation between values.

In certain embodiments, the apparatus is or comprises a monitor for obtaining information concerning the control.

In some embodiments, the system for measuring or calculating the distribution space or an approximation or changes thereof is a monitor as described in WO 2006/002685 A1. The respective disclosure of WO 2006/002685 A1 is hereby incorporated in the present application by way of reference. Of course, the present invention must not be understood to be limited to systems or monitors obtaining data by bioimpedance measurements as is described in WO 2006/002685 A1. Other bioimpedance methods known in the art and also any other methods known in the art such as dilution measurements and also any other method known to the skilled person are also contemplated and encompassed by the present invention as well.

In certain embodiments, the apparatus comprises a system or monitor for measuring Hb concentrations (e.g., in [g/dl]) and/or for determining the blood volume by the utilization of any monitor as described in "Replacement of Renal Function by Dialysis" by Drukker, Parson and Maher, Kluwer Academic Publisher, $5^{th}$ edition, 2004, Dordrecht, The Netherlands, on pages 397 to 401 ("Hemodialysis machines and monitors"), the respective disclosure of which is hereby incorporated by way of reference.

In some embodiments, the system or monitor is configured to measure the blood volume and/or the concentration of the substance—in particular Hb—by measuring an electrical conductivity.

In certain embodiments, the system or monitor is configured to measure the blood volume and/or the concentration of the substance—in particular Hb—by measuring an optical density.

In some embodiments, the system or monitor is configured to measure the blood volume and/or the concentration of the substance—in particular Hb—by measuring a viscosity.

In certain embodiments, the system or monitor is configured to measure the blood volume and/or the concentration of the substance—in particular Hb—by measuring a density.

In some embodiments, the system or monitor comprises one or more corresponding probes and/or one or more sensors for carrying out the measurements such as electrical conductivity sensors, optical sensors, viscosity sensors, density sensors, and the like.

In certain embodiments, the apparatus furthermore comprises an output device for outputting results provided by the controller.

In some embodiments, the output device is a monitor having a display, a plotter, a printer or any other system for providing an output.

In certain embodiments, the output device is connected to an actuator for controlling administration of a substance to the patient.

In other embodiments, the device may be used for treating a patient (or the patient's blood) by hemofiltration, ultrafiltration, hemodialysis, etc.

The embodiments may provide one or more of the following advantages.

In some embodiments, the present invention provides information on how the filtration rate should be controlled or fixed. The information can be advantageously used to prevent certain decreases of the patient's blood pressure caused by the dialysis. Also, the occurrence of nausea, convulsions, emesis, vertigo, impaired vision and other symptoms frequently caused by the filtration procedure can advantageously be reduced or avoided.

In certain embodiments, the present invention provides information on how high the filtration rate may be set to both prevent unwanted blood pressure drops and to accomplish the dialysis treatment as quick as possible (i.e., so as not to waste the patient's time or not to bind him to the treatment site longer than required). The latter may happen the closer the relation is to relations forming a maximum-refill curve or steady-state curve as described above.

Other aspects, features, and advantages will be apparent from the description, figures, and claims.

BRIEF DESCRIPTION OF THE DRAWINGS

In the following, the present invention is further explained by the figures of the drawing wherein same or identical elements are identified the use of identical reference numerals. However, the present invention must not be understood to be limited to the examples explained the figures.

DETAILED DESCRIPTION

Figure 1:
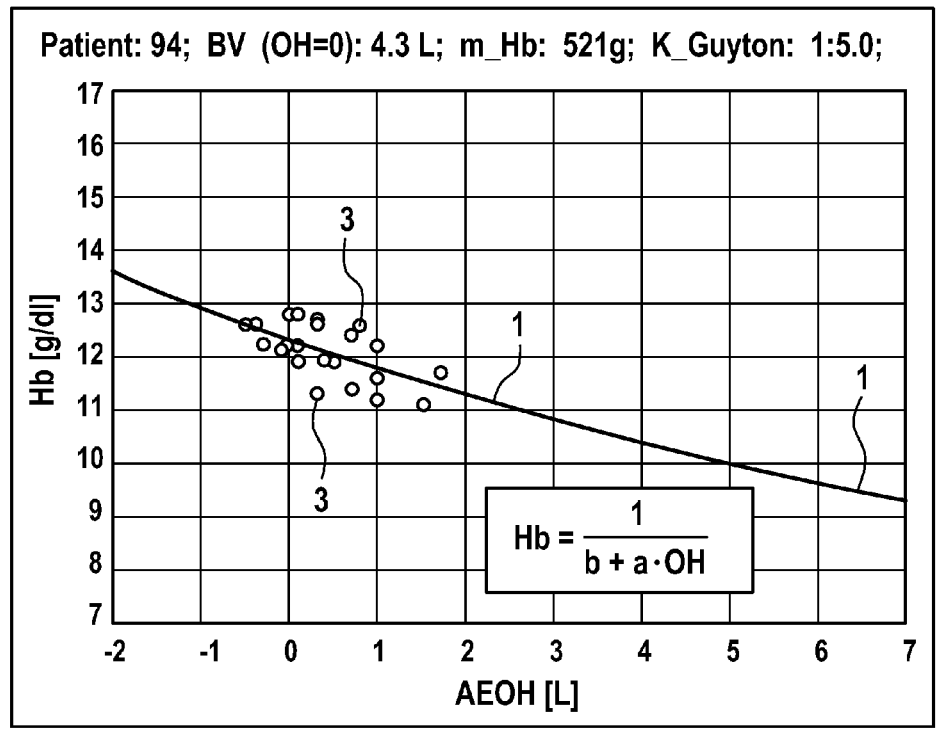
FIG. 1 shows a steady-state curve depicting the relation between the Hb-concentration and the overhydration of a dialysis patient in a diagram.

FIG. 1 shows a maximum-refill curve or steady-state curve 1 depicting the relation between the Hb-concentration (y-axis, Hb, in [g/dl]) of an anonymized dialysis patient "94" and his overhydration (x-axis, AEOH, in [liters]) at the beginning of his fluid removal treatments. Curve 1 can be gained from curve-fitting of a number of measurements 3. Measurements 3 can be gained, e.g., from measurements by utilization of monitors as disclosed in WO 2006/002685 A1.

By use of BVo, which can be measured, and by use of the parameter b, which can be approximated from FIG. 1 (see also the equations reproduced above), the total mass of Hb, ("m_Hb") can be determined.

Patient "94" has a blood volume BV of 4.3 L when measured in the normohydration state with OH=0. Further, it has been calculated that patient "94" has a total Hb mass m_Hb of 521 g.

By use of m_Hb and the parameter a, which can also be approximated or derived from FIG. 1, the slope K_Guyton of the patient's current position on the Guyton curve—with the Guyton curve being a curve depicting the blood volume BV over the extracellular fluid volume ECW of a patient explaining physiologic interdependencies between extracellular water (ECW) and the blood volume—can be determined. In FIG. 1, K_Guyton is around 1:5.0.

Figure 2:
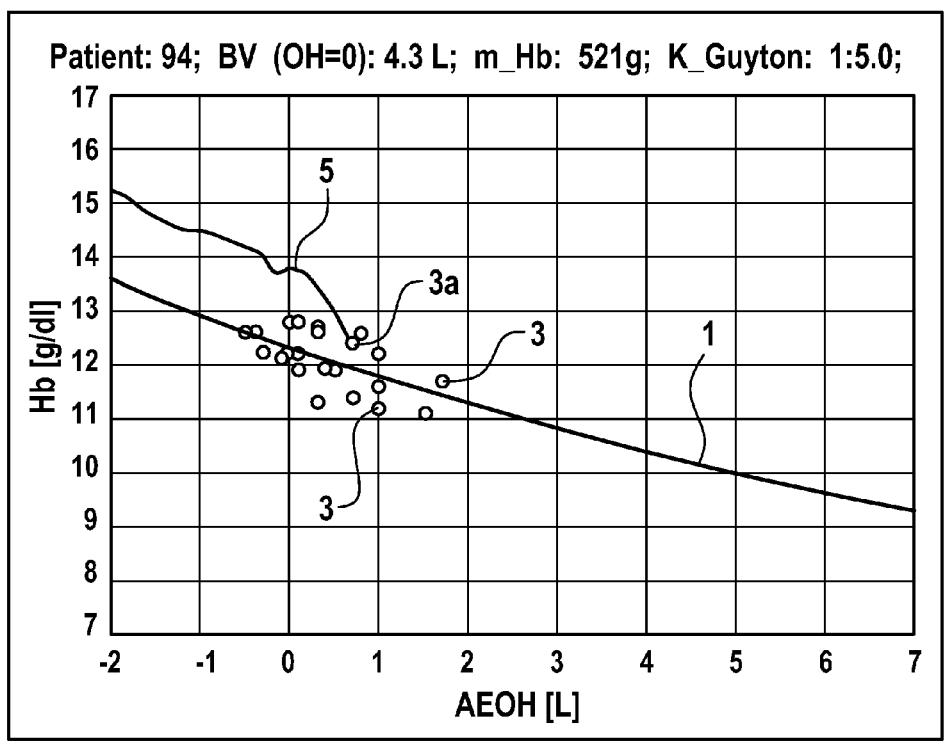
FIG. 2 shows an intradialytic course of the relation between Hb-concentration and the overhydration during dialysis in the diagram of FIG. 1.

FIG. 2 shows an intradialytic course or development of the relation between the Hb-concentration c_Hb and the overhydration AEOH of patient "94" during dialysis. In most aspects, FIG. 2 is identical to FIG. 1.

Starting from one particular measurement 3a out of the measurements 3 shown both in FIG. 1 and FIG. 2, an intradialytic curve 5 can be established during dialysis of the patient.

Curve 5 reveals the relation between Hb concentration c_Hb and the overhydration AEOH during the dialysis treatment. Since curve 5 reflects a number of measured and approximated values for the relation, curve 5 also reveals changes of the relation over time.

In case of applying very low ultrafiltration rates during dialysis, curve 5 would be identical to steady-state revealing curve 1. However, this is not shown in FIG. 2. There, curve 5 clearly deviates from curve 1.

In case curve 5 is identical to curve 1, then the refill-processes which can effect a shift from water from the interstices to the vessels of the patient have enough time to happen. For that reason curve 1 can also be named a "maximum refill curve". Obviously, in FIG. 2 the ultrafiltration rate is set too high for allowing a total refill during the course of dialysis.

Figure 3:
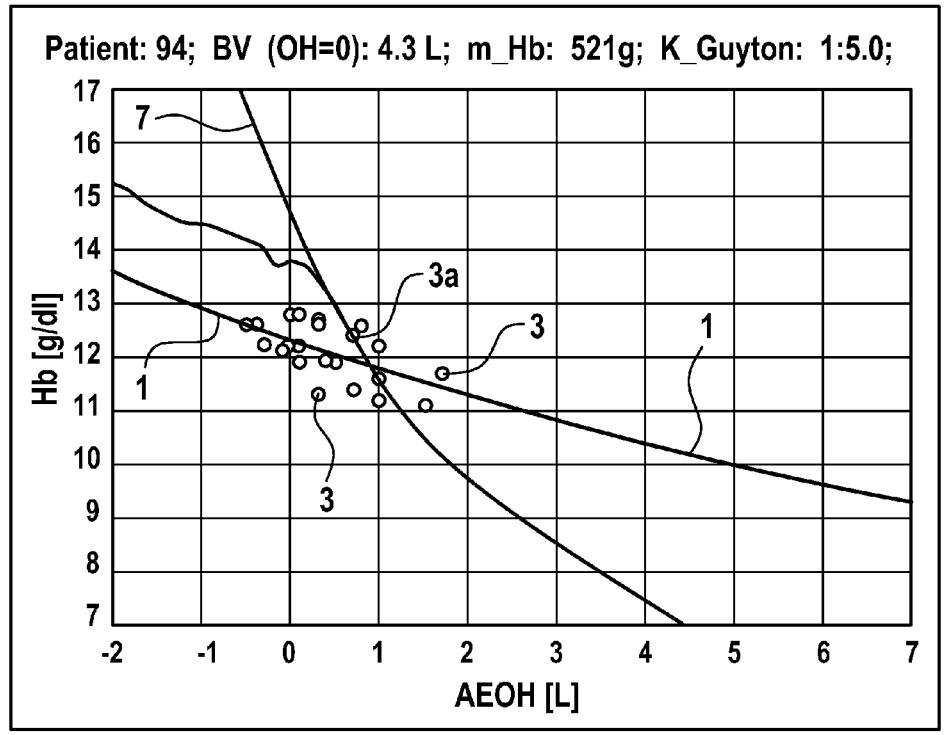
FIG. 3 additionally shows a no-refill curve in the diagram of FIG. 2.

FIG. 3 shows the diagram of FIG. 2 into which a "no-refill" curve 7, as already explained above, has been added.

The no-refill curve 7 can be calculated by use of $$Hb = \frac{m_{Hb}}{BV_{Start} - UFV}, ABOH = ABOH_{pre} - UFV \quad (5)$$

with UFV being the ultrafiltration volume, AEOHpre being the overhydration or relative overhydration measured before starting the dialysis, and BV start being the blood volume at starting the dialysis.

Figure 4:
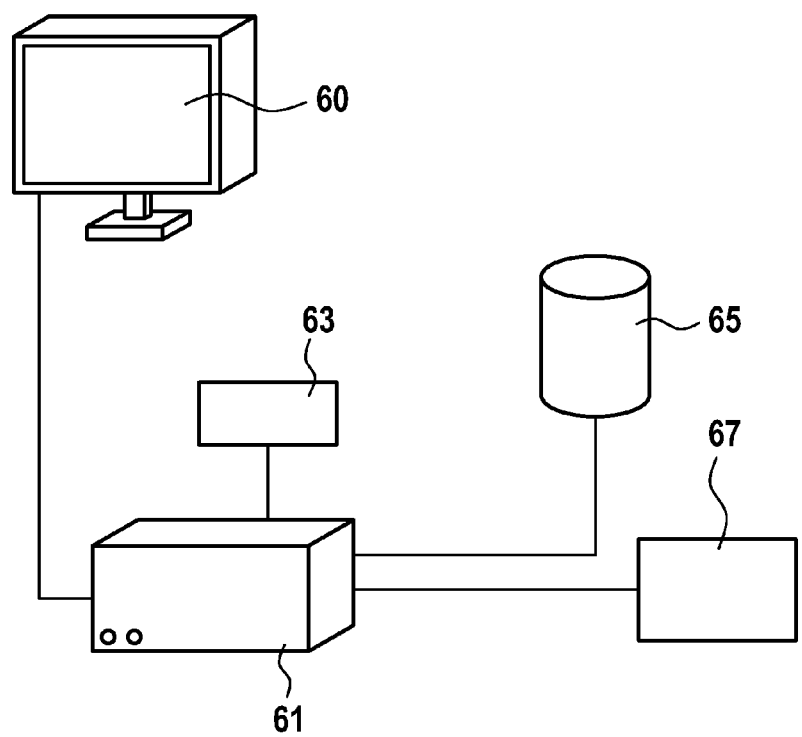
FIG. 4 shows a first apparatus comprising a controller for carrying out the method according to the present invention.

FIG. 4 shows an apparatus 61 comprising a controller 63 configured to carry out the method according to the present invention. The apparatus 61 is connected to an external database 65 comprising the results of measurements and the data needed for the method according to the present invention. The database 65 can also be an internal system of the apparatus 61. The apparatus 61 may optionally have input system 67 for inputting data into the controller 63 or into the apparatus 61 itself. Such data may be information about the size of one or more distribution spaces, the mass, the volume, the concentration of a substance as is set forth above, etc., or approximations thereof. Also, the criterion may be input by use of the input system 67. The criterion may, however, alternatively be stored in database 65 or any other storage system. The criterion may be calculated or determined by the controller 63 or any other item comprised by the apparatus 61 or interconnected to it. The results of the evaluation, calculation, comparison, assessment etc. performed by the controller 63 and/or the apparatus 61 can be displayed on a monitor 60 or plotted by utilization of a—not displayed but optionally also encompassed—plotter or stored by utilization of the database 65 or any other storage system. The database 65 can also comprise a computer program initiating the method according to the present invention when executed.

In particular, the controller 63 can be configured for determining a value reflecting the distribution of the fluid, and for assessing whether the relation fulfils at least one criterion.

Figure 5:
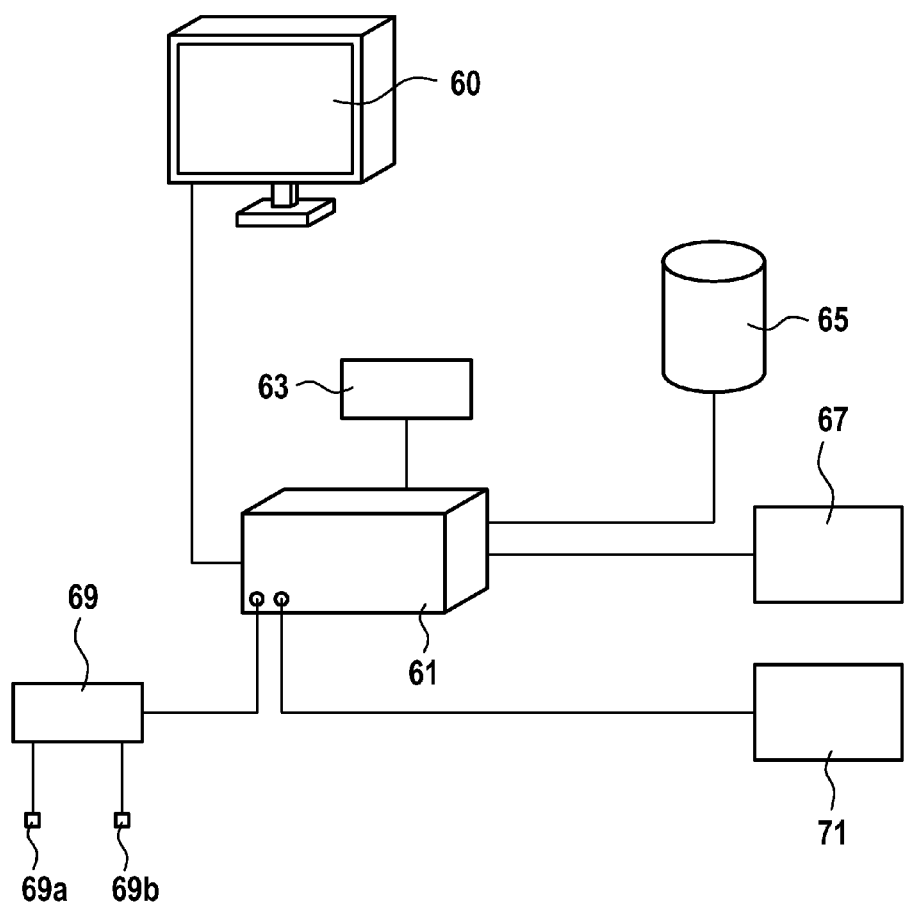
FIG. 5 shows a second apparatus comprising a controller for carrying out the method according to the present invention.

As can be seen from FIG. 5, for corresponding measurements, the apparatus 61 can be connected (by use of wires or wireless) with a bioimpedance measurement system 69 as one example of a system for measuring or calculating the distribution or the size(s) of one or more distribution spaces or approximations or changes thereof. Generally, the system for measuring or calculating can be provided in addition to the external database 65 comprising the results of measurements and the data needed for the method according to the present invention, or in place of the external database 65 (that is, as an substitute).

The bioimpedance measurement system 69 can be capable of automatically compensating for influences on the impedance data like contact resistances.

An example for such a bioimpedance measurement system 69 is a device from Xitron Technologies, distributed under the trademark Hydra™ that is further described in WO 92/19153, the disclosure of which is hereby explicitly incorporated into the present application by reference.

The bioimpedance measurement system 69 may comprise various electrodes. In FIG. 5, only two electrodes 69a and 69b are shown which are attached to the bioimpedance measurement system 69. Additional electrodes are, of course, also contemplated.

Each electrode implied can comprise two or more ("sub"-) electrodes in turn. Electrodes can comprise a current injection ("sub-")electrode and a voltage measurement ("sub-")electrode. That is, the electrodes 69a and 69b shown in FIG. 5 can comprise two injection electrodes and two voltage measurement electrodes (i.e., four electrodes in total).

Generally spoken, the apparatus according to the present invention can be provided with systems such as a weighing system, a keyboard, a touch screen etc. for inputting the required data, sensors, interconnections or communication links with a lab, any other input system, etc.

Similarly, the apparatus 61 may have a further system 71 for measuring or calculating for obtaining a value reflecting the distribution of another distribution space and/or for obtaining values reflecting the mass, the volume or the concentration of the substance that can be provided in addition to the external database 65 or in place of the external database 65 (that is, as an substitute).

The system 71 can be provided as a weighing system, a keyboard, a touch screen etc. for inputting the required data, sensors, interconnections or communication links with a lab, a Hb (or any other substance suitable for measuring, calculating or approximating the size of a distribution space) concentration probe, any other input, etc.

Figure 6:
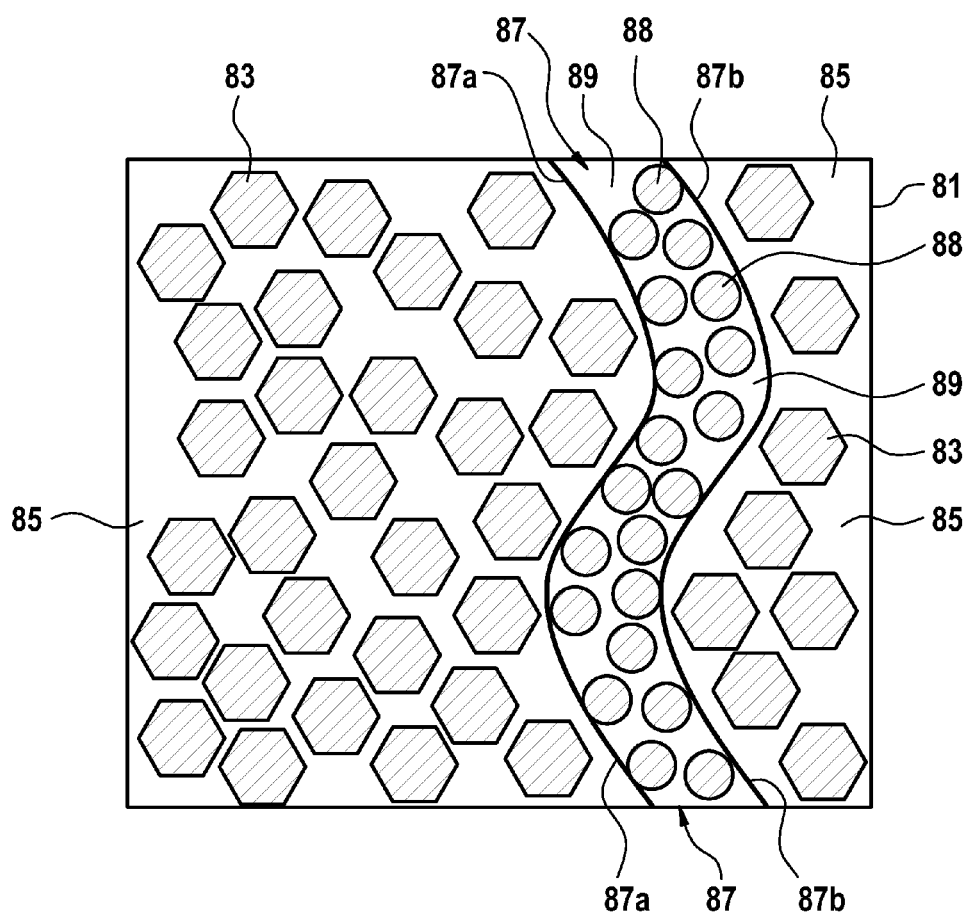
FIG. 6 shows a schematic cut through body tissue for defining certain terms relating to distribution spaces as used within the present specification.

FIG. 6 shows a schematic cut through body tissue for defining certain terms relating to distribution spaces as used within the present specification.

In particular, FIG. 6 shows a defined volume 81 comprising tissue cells 83 comprising intracellular water, an interstitium 85 comprising extracellular water, and a blood vessel 87 with cut vessel walls 87a and 87b.

The blood vessel comprises blood cells 88 (comprising intracellular water). The blood cells are embedded into blood plasma 89 (comprising extracellular water).

Figure 7:
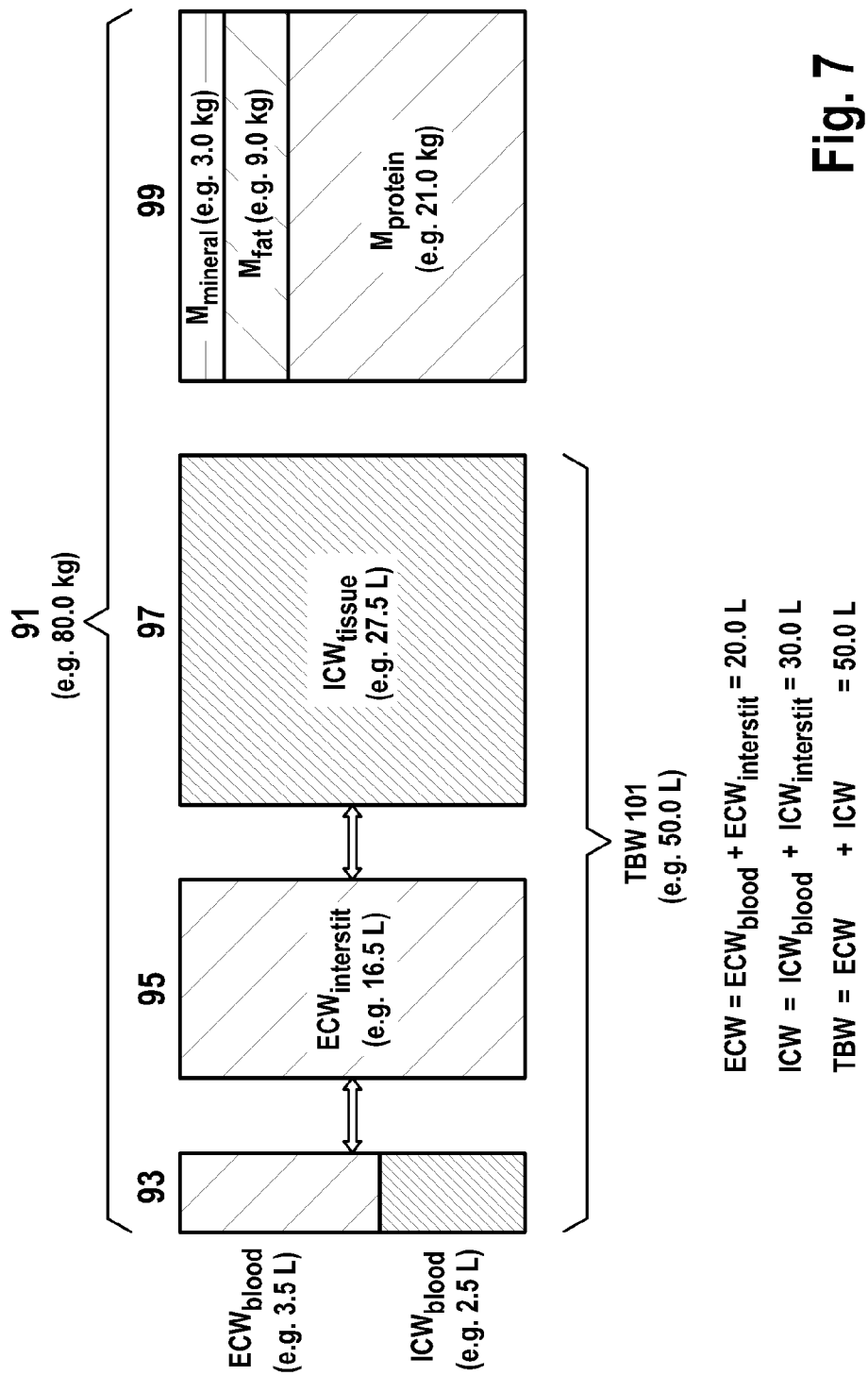
FIG. 7 shows an example of how certain terms relating to distribution spaces may be understood in terms of the present invention and how certain distribution spaces may be interconnected by of a general concept.

FIG. 7 shows an example of how certain terms relating to distribution spaces may be understood in terms of the present invention. It also shows how certain distribution spaces may be interconnected by use of a general concept.

As can be seen from FIG. 7, the whole body weight 91—which can amount to, for example, 80.0 kg—can be understood as the sum of the blood volume (BV) 93, the water in the interstitium (extracellular) (ECWinterstit) 95, the water in the cells of the tissue (intracellular) (ICWtissue) 97, and the solid components of the body 99.

The blood volume may be understood as the sum of the extracellular water that is present within the vessels (ECWblood), in particular in the blood plasma, and the intracellular water (ICWblood) that is present in the vessel or the (red) blood cells. In an example, the ECWblood may be 3.5 L, the ICW may be 2.5 L, the blood volume 93 may be 6.0 L.

The water in the interstitium (extracellular) 95 (ECWinterstit) can encompass 16.5 L. The water in the cells of the tissue (intracellular) 97 (ICWtissue) can encompass 27.5 L.

The solid components 99 of the body comprise the mineral mass Mmineral which can have 3.0 kg, the fat mass Mfat which can be 9.0 kg, and the protein mass Mprotein which can amount to 21.0 kg. The solid components 99 can thus amount to 33.0 kg.

As can be seen from FIG. 7, the sum of the blood volume 93, the water in the interstitium (extracelluar) 95, and the water in the cells of the tissue (intracellular) 97 can be understood as the total body water 101 (TBW). The total body water 101 can encompass 50.0 L.

As can further be seen from FIG. 7, the sum of the total body water 101 and the solid components 99 can be equal to the whole body weight 91.

As is readily understood by the skilled one, the above given figures and weights are to be understood as examples which may be found in one particular patient, whereas other patients may reveal different weights and mass contributions. However, FIGS. 6 and 7 are well suited for giving one example of how certain terms regarding to distribution spaces may be understood, and also how certain distribution spaces of a patient's body relate to each other.

Again, it is noted that all or at least some of the figures relate to Hb/anemia state and volume or weight/hydration state by use of examples showing how one particular embodiment according to the present invention may be carried out. They are not to be understood as limiting.

Figure 8:
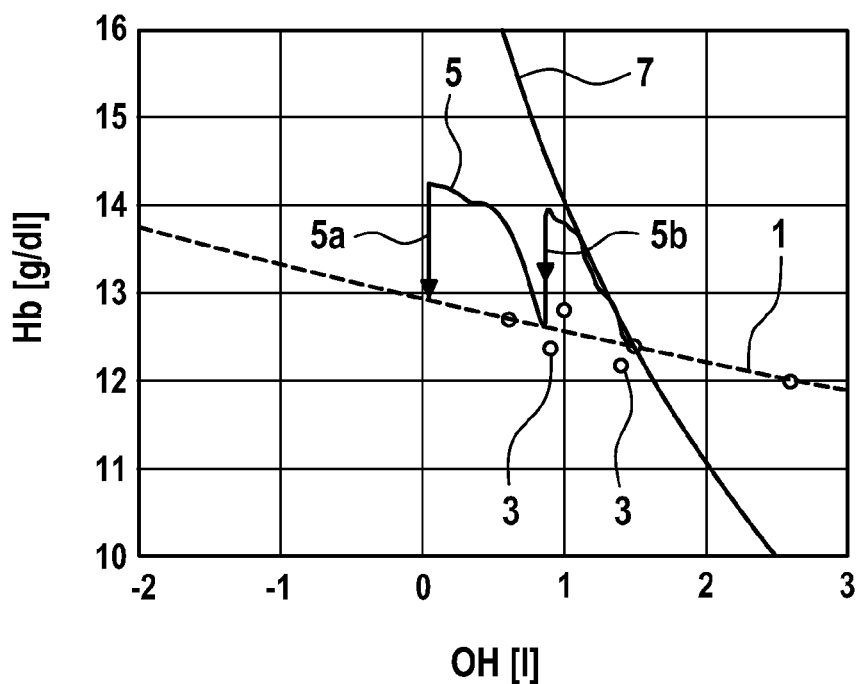
FIG. 8 shows the intradialytic course of a patient's hemoglobin/overhydration relation.

FIG. 8 shows the intradialytic (i.e., during dialysis) development of a relation between hemoglobin concentration and overhydration of a particular patient, the development being identified as curve 5.

As can readily be understood, the course of the steady state revealing curve 1 can be determined by interrupting the treatment of the patient during one treatment session for a time span and continuing same, or by comparing data from several, at least two, treatment sessions. Following the interruption during the one treatment session or following the termination of the first treatment session out of several ones, the Hb concentration will decrease due to the refill-effect (as described above). In FIG. 8, such decrease can be observed twice and is depicted by use of reference numerals 5a and 5b. The time span may last until the Hb concentration does not change any more or at least that long.

As is evident, by use of two or more interruptions as described before, the steady state revealing curve 1 can be determined. Also, by use of one or more such interruptions, the validity of an earlier determined curve 1 can be assessed. For example, the course of the earlier determined curve 1 can be assessed by checking whether the decline of curve 5 (or portions 5a, 5b thereof, in particular) ends at or with an intersection of portion 5a or 5b (or similar portions which correspond to a decrease) with the steady state revealing curve 1.

Again, the idea explained with reference to FIG. 8 or any other figure attached hereto is not limited to Hb and OH. Any other parameter that might replace Hb and OH in the light of the present disclosure may also be used to find or confirm a steady state revealing curve.

Figure 9:
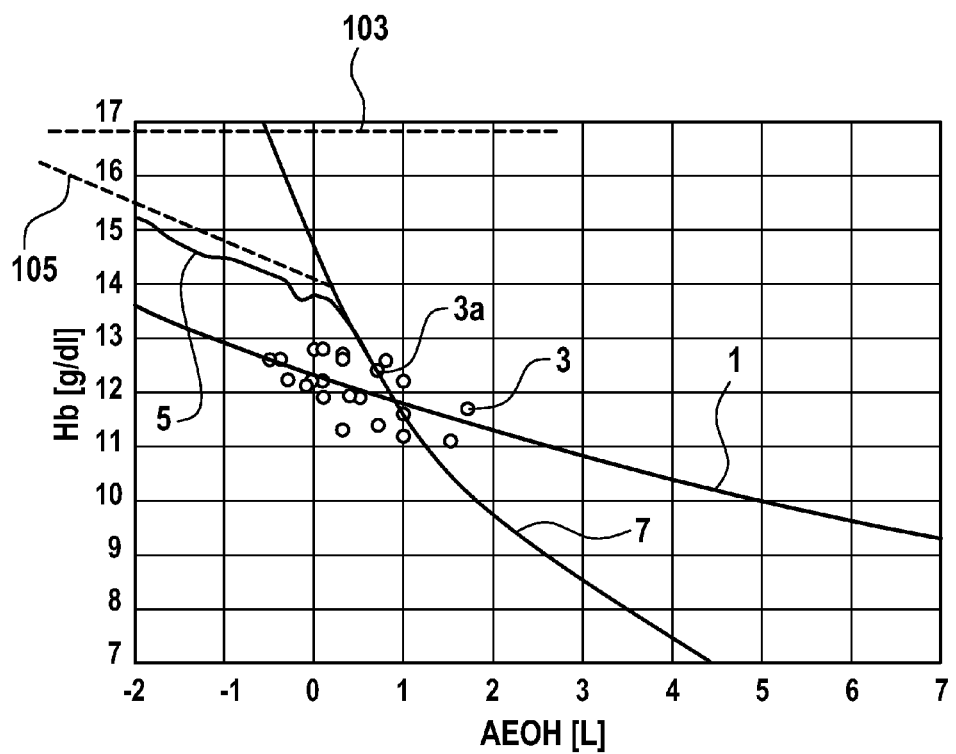
FIG. 9 shows a threshold and a trajectory for a dialysis by of ultrafiltration, illustrated in the diagram of FIG. 2.

FIG. 9 shows a threshold 103 and a trajectory 105, both being illustrated as broken or dashed lines, illustrated in the diagram known from FIG. 2 reflecting the course of an ultrafiltration treatment.

Both the threshold 103 and the trajectory 105 can be used—either together or taken alone—for controlling the treatment according to the present invention as is explained in the following example, the example being related to a body fluid treatment ultrafiltration.

As can be seen from FIG. 9, intradialytic ultrafiltration control can be improved by observing a maximum Hb concentration of the patient's blood during dialysis, the maximum Hb concentration being indicated by the threshold 103. In some embodiments of the present invention, the dialysis process may be stopped once the intradialytic curve 5 indicating the intradialytic blood volume has crossed the threshold 103, is about to cross it or has crossed it for longer than a predetermined span of time, or the like.

If, for example, the minimum or minimum absolute blood volume BV should not drop below, say, 4 liters (L), the threshold 103 may set to 16.7 g/dl (or g/(dL)) under the assumption that the mass of Hb is known, following from that facts that in the present example the mass of Hb amounts to 500 g, and that BVmin shall be 3 L or 30 dl (dL). Then, the maximum Hb concentration 16.7 g/dl is given by 500 g divided by 30 dl=16.7 g/dl.

Also, a threshold can be chosen parallel to or in a certain, predetermined distance to the steady state revealing curve 1. The distance may be uniform or equidistant, or the distance may differ. The distance may vary depending on further data, measurements or values, including ones that also may vary. For example, the distance may be set to be a fixed value. The fixed value may be, e.g., 2 g/dl. In this example, the threshold runs 2 g/dl above curve 1.

Also, in certain embodiments, the dialysis process may be controlled such that the trajectory 105 is followed exactly, or as close as possible, or within a certain range or approximation or the like.

For example, in some embodiments, the dialysis process may be controlled such that the intradialytic curve 5 preferably follows the no-refill curve 7 during treatment for a certain time or a predetermined period of time, for example 30 min after the treatment has been started. If the intradialytic curve 5 does not leave the no-refill curve 7 (or stays at least within certain limits) or remains within a predetermined range given for the no-refill curve 7 within those 30 min, then the set ultrafiltration rate might be considered as appropriate.

However, if the intradialytic curve 5 should behave differently, this may be taken as an indication that the ultrafiltration rate be better decreased.

In another attempt to control the ultrafiltration treatment, the ultrafiltration rate may be set such that a certain first trajectory (or a certain part thereof), which may, e.g., be in parallel to the no-refill curve 7, be followed before another trajectory or another part of the first trajectory, which may, e.g., run in parallel to the steady state revealing curve 1 or at a constant Hb concentration level, is followed. For example, the ultrafiltration rate may be set such that first the no-refill curve 7 is followed and later a trajectory such as trajectory 105 is followed.

In again another attempt to control the ultrafiltration treatment it may be ensured that the intradialytic curve 5 never exceeds an absolute Hb concentration limit which may be represented by a threshold such as the threshold 103, irrespective of the patient's blood volume, or does, if the limit is exceeded, meet certain conditions.

Besides, once the Hb concentration has risen from initial value by a set, fixed or predetermined difference of, e.g., 2 g/dl (for example from 11 g/dl to 13 g/dl), in certain embodiments ultrafiltration rate is controlled such that the Hb concentration is maintained at, for example, 13 g/dl. That implies constant blood volume BV with the ultrafiltration rate and the refill effect being balanced.

Finally, a critical blood volume, which may lead to the termination or interruption of the treatment if under-run, may be determined by making repeated blood pressure measurements during the treatment (e.g., dialysis). If the blood pressure should fall below a certain value, the blood volume existing at that point of time can be contemplated or set as the minimal or critical blood volume.

Figure 10:
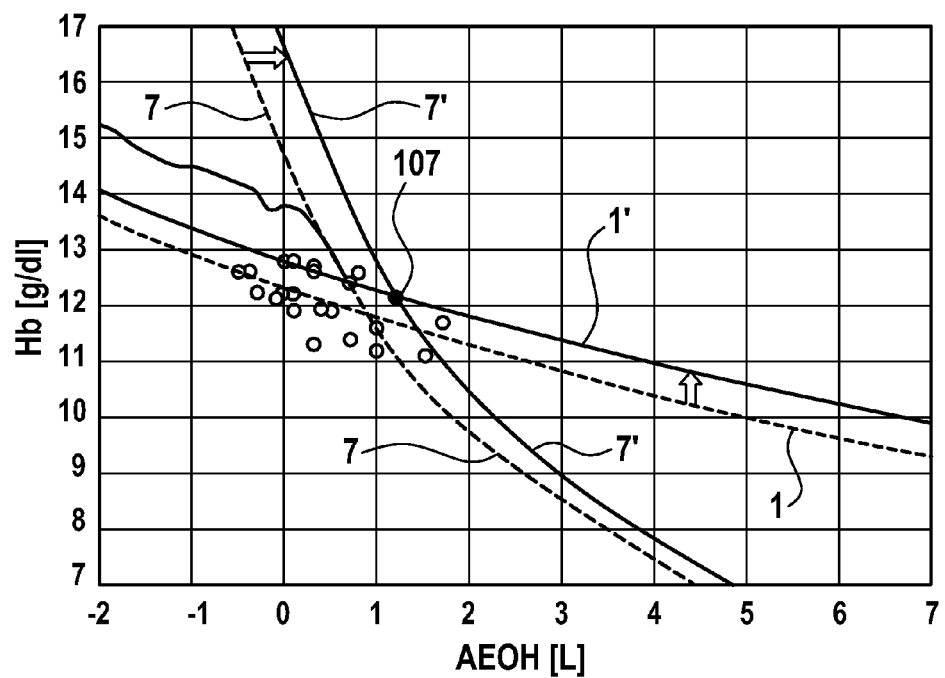
FIG. 10 shows shifted a steady state revealing curve and a shifted no-refill curve illustrated in the diagram of FIG. 2.

FIG. 10 is based on the diagram known from FIG. 2 or FIG. 3 and reveals a steady state revealing curve 1 and a no-refill curve 7.

As has been explained above with respect to FIG. 9, in certain embodiments according to the present invention the steady state revealing curve 1 and/or the no-refill curve 7 shown also in FIG. 10 may be used for controlling the treatment in that the filtration machine is controlled such that the intradialytic curve 5 follows a trajectory (not shown in FIG. 10).

Both the steady state revealing curve 1 and the no-refill curve 7 have to be adapted to or to be calculated based on variable parameters which have to be determined or measured before starting the treatment session at issue on the day of the treatment itself. The course and the morphology of the no-refill curve 7 depends on the Hb mass (m_Hb) and the blood volume BVo right before starting the treatment. In addition to these parameters, the course and the morphology of the steady state revealing curve 1 depend also on the overhydration and the Guyton factor. Due to measurement errors and slight changes in the physiologic steady state curve parameters (Hb mass, Guyton factor, BVo), on the treatment day the starting point will normally not lie exactly on the steady state curve, but slightly aside.

Therefore, the present invention proposes to approximate shift curves 1' and/or 7' by vertically shifting curve 1 and/or by horizontally shifting curve 7 as shown in the diagram of FIG. 10 such that both of them start from a starting point 107 which can be measured as described above. This shifting allows to take advantage of starting into the treatment with an approximated steady state revealing curve 1' and/or an approximated no-refill curve 7', both curves 1' and 7' starting from the correct starting point 107 of the curves for the treatment in question, and both curves 1' and 7' having a probably highly reliable morphology. This approximation can be carried out quickly and without remarkable effort.

Figure 11:
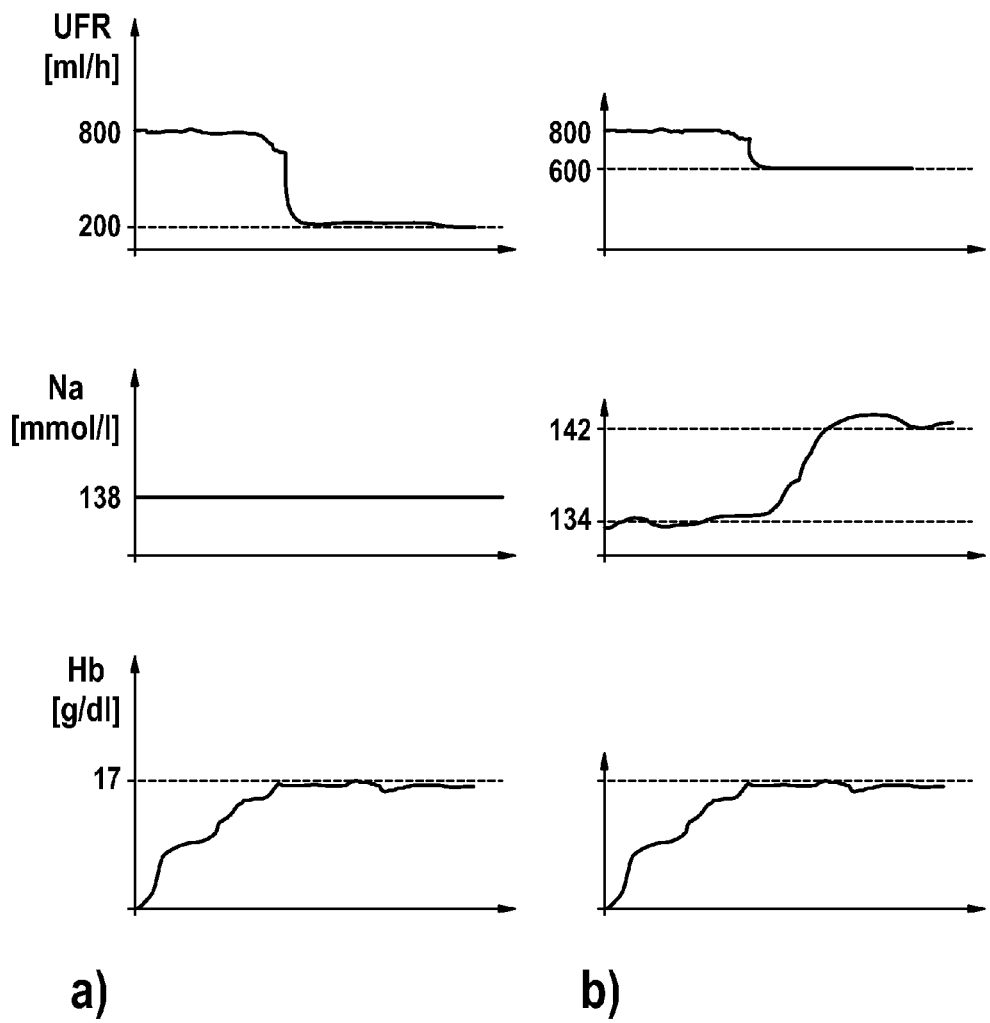
FIG. 11 shows an interrelation between the ultrafiltration rate and the sodium concentration.

FIG. 11 shows an interrelation between the ultrafiltration rate and the sodium concentration during a dialysis treatment. The interrelation is explained by two examples a) and b).

As can be seen from example a) of FIG. 11, increasing the sodium concentration (measured in the patient's blood as one example of a distribution space) obviously results in an increased refilling from the interstices towards and into the blood vessels. In FIG. 11, example b) represents the case in which sodium concentration is increased to over 142 mmol/l, whereas example a) represents the case where the sodium concentration is kept constant at 138 mmol/l. As can be seen from FIG. 11, once the Hb concentration has reached a certain level (here: 17 g/l), in example b) the ultrafiltration rate needs not to be decreased in the same manner as in example a) to avoid further increasing of Hb or even exceeding of the Hb concentration level or limit. In other words, a higher sodium concentration—during an early or a late stage of the treatment—may contribute to a higher refill. The higher refill, in turn, may advantageously allow to continue dialysis or treatment in general with a higher ultrafiltration rate again, at an earlier or a later stage of the treatment. Generally spoken, adapting of the patient's sodium concentration measured in blood may be used to control the filtration.

Therefore, in certain embodiments according to the present invention, the method comprises the step of controlling and/or amending the dialysate and/or the extracorporeal blood with respect to the sodium—or any other suitable substance that contributes to the oncotic pressure of the fluid it is comprised by—concentration during treatment.

Correspondingly, in some embodiments according to the present invention, the devices comprise a system to carry out the step of controlling and/or amending the concentration of sodium referred to above.

In certain embodiments, the sodium concentration is set via the sodium concentration of the dialysate or the substituate. In some embodiments, the sodium concentration of the dialysate or the substituate is controlled or amended.

With respect to the present invention, in some embodiments, the refilling process is, in particular additionally, adjusted or at least influenced by utilization of the sodium concentration.

In certain embodiments, the concentration of sodium or the like (that is, of any oncotic pressure effective substance) in the extracorporeal blood, in the substituate or in the dialysate is controlled such that a non-constant concentration over the treatment session is achieved and aimed at.

In this respect it is noted that the present invention is not limited to increasing the sodium concentration towards the end of the treatment or only having achieved a certain Hb concentration level. Rather, the present invention also relates to increasing the sodium concentration before having reached a certain or pre-set Hb concentration, or after having reached it.

Also, the present invention is not limited to decreasing the sodium concentration at the beginning of the treatment below, e.g., 138 mmol/ml as it is the case in example b) of FIG. 11. Rather, even when it is contemplated to increase the concentration of the oncotic effective substance later on, the treatment may be started with a typical concentration thereof such as 138 mmol/l in the example of sodium.

In addition or alternatively, the sodium concentration is brought to a higher level before reaching a pre-determined top level of the Hb concentration to make sure that by utilization of the so increased refill an upper Hb concentration level or limit (here: 17 dg/l) is not reached early—which allows to apply a higher filtration rate during these early stages—and to lower the sodium concentration towards a later stage of the treatment to withdraw oncotic effect salts such as sodium from the blood again.

Also, in some embodiments according to the present invention, the controller is configured to carry out a method or control it as explained above with reference to FIG. 11. Also, the device according to the present invention may encompass system(s) other than the controller to carry out one or more of the methods explained with respect to FIG. 11.

Again it is to be noted that the examples given above, in particular if based on the discussed figures, are not limited to the monitoring of Hb or OH during dialysis. Rather, above teaching and in particular the teaching of the figures is contemplated also for parameters other than Hb and/or OH, the parameter being monitored during any treatment, not only dialysis. In any case, the examples of the figures are chosen only for illustration purposes.

What is claimed is:

1. A method for controlling a filtration rate during treatment of a bodily fluid of a patient by utilization of a bodily fluid treatment device, comprising the steps of:
    defining a target relation or a development of the target relation between at least one calculated or measured value reflecting:
        (a) a mass or a concentration or a volume of a substance comprised by a tissue or the bodily fluid of the patient or an approximation thereof, and
        (b) a distribution space of the patient or an approximation thereof;
    during treatment of the bodily fluid, repeatedly calculating or measuring values reflecting at least one of:
        the mass or the concentration or the volume of the substance, or
        the distribution space or an approximation thereof, determining a relation between the calculated or measured values at least once; and
    controlling the filtration rate of the bodily fluid treatment device such that the determined relation is or approaches the target relation.

2. The method according to claim 1, wherein the values reflecting the mass, the volume or the concentration of the substance are obtained from blood samples.

3. The method according to claim 1, wherein the substance is selected from the group consisting of: hemoglobin, albumin, insulin, glucose, c-reactive protein (CRP), and pharmaceutically effective substances.

4. The method according to claim 1, wherein the mass, the volume or the concentration of the substance or changes thereof is an indicator of an anemia state of the patient.

5. The method according to claim 4, wherein the indicator of the anemia state of the patient is a concentration of hemoglobin, a total mass of hemoglobin or a change over time of hemoglobin, or is a hematocrit or a change over time of the hematocrit.

6. The method according claim 1, wherein the distribution space of the patient is a measured or a calculated value of a volume of blood.

7. The method according to claim 1, wherein the distribution space of the patient is an approximation based on either measured or calculated values reflecting a relative overhydration of the patient.

8. The method according to claim 1, further comprising the step of:
    defining a target range for the target relation in a diagram reflecting (a) the mass or the concentration or the volume of the substance or an approximation thereof and (b) the distribution space or the approximation thereof.

9. The method according to claim 1, further comprising the step of:
    calculating a no-refill-curve.

10. The method according to claim 1, further comprising the step of:
    at least one of calculating or measuring the values reflecting at least one of (a) the mass or the concentration of the substance or an approximation thereof or the distribution space of the patient or an approximation thereof.

11. The method according to claim 1, further comprising the step of:
    at least one of controlling or amending a concentration of an oncotic pressure effective substance comprised by at least one of a dialysate, a substituate in the dialysate, or a substituate blood during treatment to increase a refill process or a refill rate during at least one part of the treatment of the bodily fluid.

12. A filtration rate controlling system configured to carry out the method according to claim 1, the system having a controller comprising:
    a target relation defining system configured to define a target relation or a development of the target relation between at least one calculated or measured value reflecting:
        (a) a mass or a concentration or a volume of a substance comprised by a tissue or the bodily fluid of the patient or an approximation thereof, and
        (b) a distribution space of the patient or an approximation thereof;
    a calculation system configured to, during treatment of the bodily fluid, repeatedly calculate values reflecting at least one of:
        the mass or the concentration or the volume of the substance, or
        the distribution space or an approximation thereof, and configured to determine a relation between the calculated or measured values at least once; and
    a signal output system configured to output at least one signal to a controlling system configured to control the filtration rate of a bodily fluid treatment device such that the determined relation is or approaches the target relation.

13. The filtration rate controlling system according to claim 12, further comprising at least one system selected from the group consisting of:
    a target range defining system configured to define a target range for the target relation in a diagram reflecting (a) the mass or the concentration of the substance or an approximation thereof and (b) the distribution space or the approximation thereof;
    a no-refill-curve calculating system configured to calculate a no-refill-curve; and
    at least one of a calculating or a measuring system configured to calculate or measure at least one value reflecting at least one of the mass or the concentration of the substance or the distribution space of the patient or an approximation thereof.

14. The filtration rate controlling system according to claim 12 further comprising at least one system selected from the group consisting of:
    a system configured to obtain at least one value reflecting the distribution space or an approximation of the distribution space or changes of the distribution space of the patient's body; and a system configured to obtain a value reflecting the mass, the volume or the concentration of the substance or changes thereof.

15. The filtration rate controlling system according to claim 14, further comprising:
a system configured to measure or calculate the distribution space or an approximation or changes of the distribution space, or wherein the system configured to obtain at least one value consists of the system configured to measure or calculate.

16. The filtration rate controlling system according to claim 14, wherein the system configured to obtain at least one value reflecting the mass, the volume or the concentration of the substance comprises at least one of a weight system, a system for determining the blood volume of the patient, a keyboard, a touch screen, a system for measuring or calculating at least one of the concentration, the volume or the mass of the substance, or changes thereof, or wherein the system configured to obtain at least one value consists of the system for configured to measure or calculate.

17. The filtration rate controlling system according to claim 14, further comprising:
a system configured to determine or assess the relation between values.

18. A device for treating a patient's blood, comprising at least one filtration rate controlling system according to claim 12.

19. The device for treating a patient's blood according to claim 18, wherein the device is configured to treat a patient by at least one of dialysis, hemofiltration, ultrafiltration, or hemodialysis.

20. A non-transitory computer-readable storage medium with an executable program stored thereon, wherein the program instructs a programmable computer system so as to execute the steps of the method according to claim 1.

* * * * *